(12) United States Patent
Alberico et al.

(10) Patent No.: US 9,403,864 B2
(45) Date of Patent: Aug. 2, 2016

(54) PROCESS FOR THE SYNTHESIS OF CARBONUCLEOSIDE AND INTERMEDIATES FOR USE THEREIN

(75) Inventors: Dino Alberico, Mississauga (CA); Joshua Clayton, Stoney Creek (CA); Craig Dixon, Brooklin (CA); Boris Gorin, Oakville (CA)

(73) Assignee: Alphora Research Inc., Ontario (CA)

( * ) Notice: Subject to any disclaimer, the term of this patent is extended or adjusted under 35 U.S.C. 154(b) by 111 days.

(21) Appl. No.: 13/700,259

(22) PCT Filed: May 30, 2011

(86) PCT No.: PCT/CA2011/050323
§ 371 (c)(1),
(2), (4) Date: Feb. 19, 2013

(87) PCT Pub. No.: WO2011/150512
PCT Pub. Date: Dec. 8, 2011

(65) Prior Publication Data
US 2013/0144058 A1    Jun. 6, 2013

(30) Foreign Application Priority Data

May 31, 2010   (CA) ..................................... 2705953
Feb. 3, 2011   (CA) ..................................... 2730622

(51) Int. Cl.
*C07D 473/18*   (2006.01)
*C07H 19/16*    (2006.01)
*C07D 319/08*   (2006.01)
*C07D 493/04*   (2006.01)

(52) U.S. Cl.
CPC .............. *C07H 19/16* (2013.01); *C07D 319/08* (2013.01); *C07D 473/18* (2013.01); *C07D 493/04* (2013.01); *Y02P 20/55* (2015.11)

(58) Field of Classification Search
CPC .................................................... C07D 473/18
USPC ......................................................... 544/276
See application file for complete search history.

(56) References Cited

U.S. PATENT DOCUMENTS

| 5,206,244 A | 4/1993 | Zahler et al. | |
| 2011/0201809 A1* | 8/2011 | Hu et al. | 544/276 |

FOREIGN PATENT DOCUMENTS

| CA | 2 705 953 A1 | 11/2011 |
| CN | 1566118 | 1/2005 |

(Continued)

OTHER PUBLICATIONS

Wuts, P. G. M. and Greene, T. W. (2006) Protection for the Hydroxyl Group, Including 1,2- and 1,3-Diols, in Greene's Protective Groups in Organic Synthesis, Fourth Edition, John Wiley & Sons, Inc., Hoboken, NJ, USA.*

(Continued)

Primary Examiner — Golam M M Shameem
Assistant Examiner — Laura Daniel
(74) Attorney, Agent, or Firm — Jenkins, Wilson, Taylor & Hunt, P.A.

(57) ABSTRACT

Disclosed is a process for preparing a carbonucleoside of formula (1) and intermediates for use therein. The process involves the step of reacting a compound of formula (2) with a compound of formula (3) under Mitsunobu-type reaction conditions to obtain a compound of formula (4), wherein $PG_1$, $PG_2$, $PG_3$ and $PG_4$ are protecting groups. The compound of formula (4) is deprotected to form the compound of formula (1), as shown below.

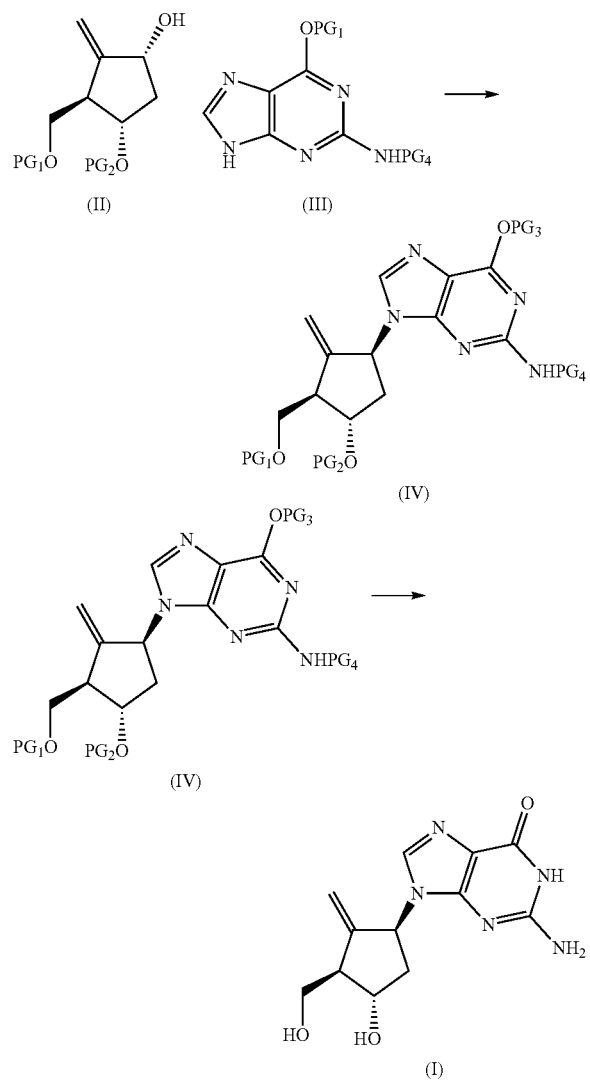

22 Claims, No Drawings

(56) References Cited

FOREIGN PATENT DOCUMENTS

| | | |
|---|---|---|
| CN | 101235034 | 8/2008 |
| CN | 101805339 | 8/2010 |
| CN | 102958931 | 3/2013 |
| JP | 2229192 | 9/1990 |
| WO | WO03/051881 | 6/2003 |
| WO | WO2004/052310 | 6/2004 |
| WO | WO2011/150012 | 12/2011 |
| WO | WO2011/150512 | 12/2011 |
| WO | WO2012/006964 | 1/2012 |

OTHER PUBLICATIONS

Tsunoda, Tetsuto. Tetrahedron Letters, 37:14 (1996). 2459-2462.*
Kocienski, Philip. Protecting Groups. 3rd Ed. Thieme. (2005) 4-6.*
International Search Report corresponding to International Application No. PCT/CA2011/050323 dated Aug. 29, 2011.
Fletcher et al., "Concise access to N9-mono-, N2-mono- and N2,N9-di-substituted guanines via efficient Mitsunobu reactions," Tetrahedron 66 pgs.: 4621-4632 (2010).
Notification Concerning Transmittal of International Preliminary Report on Patentability (Chapter I of the Patent Cooperation Treaty) corresponding to International Patent Application No. PCT/CA2011/050323 dated Dec. 13, 2012.
Notification of Transmittal of the International Search Report and the Written Opinion of the International Searching Authority corresponding to International Patent Application No. PCT/CA2011/050323 dated Aug. 29, 2011.
"Recently Modified Mitsunobu Reactions," TCI Product Literature (6 pages) (2007).
Dey, S., and Garner, P., "Synthesis of tert-Butoxycarbonyl (Boc)-Protected Purines," The Journal of Organic Chemistry. vol. 65, No. 22, pp. 7697-7699 (2000).
Schenck, C.L., and Nadeau, J.M., "Synthesis and redox properties of racemic electroactive polymers containing axially chiral adamantyl segments," Tetrahedron. vol. 66, No. 2, pp. 462-466 (2010).

* cited by examiner

PROCESS FOR THE SYNTHESIS OF CARBONUCLEOSIDE AND INTERMEDIATES FOR USE THEREIN

CROSS-REFERENCE TO RELATED APPLICATION

This application claims the benefit of and priority to Canadian Patent Application Nos. 2,705,953 and 2,730,622 filed May 31, 2010 and Feb. 3, 2011 respectively.

The content of the above patent applications are hereby expressly incorporated by reference into the detailed description hereof.

TECHNICAL FIELD

This specification relates to a process for synthesis of carbonucleoside and intermediates for use therein.

BACKGROUND

Entecavir (structural formula 1, shown below) is an antiviral compound used in the treatment of hepatitis B infections in humans. It is marketed under the trade name "Baraclude", as oral tablets and solutions.

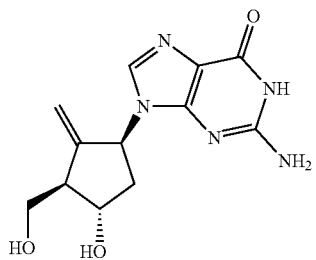

Prior art methods of making entecavir involve protection of hydroxyl and hydroxymethyl groups on a cyclopentane starting material with silyl protecting groups; while chemical reaction and derivatization of other groups to form the entecavir molecule are conducted. The silyl protecting groups are removed by hydrolysis in a final or close to final synthetic process step.

Canadian Patent Application No. 2,705,953, incorporated herein by reference, discloses a process for preparation of entecavir and similar carbonucleoside compounds, which avoids the use of such silyl protecting groups.

In the preparation of carbonucleosides, coupling using guanine can be challenging and can lead to carbonucleosides having different stereochemistry. Moreover, use of guanine in forming carbonucleosides can lead to undesired side-products, such as, coupling of the guanine at the N2, N7 or O6 position rather than at the N9 position. These side products can be difficult to isolate and purify from the N9 product. This is addressed to some extent by using a guanine derivative that has a halide, such as chlorine or iodine, at the O6-position, to obtain an intermediate carbonucleoside. This intermediate carbonucleoside is further reacted to obtain the guanine based carbonucleoside. However, such a procedure does not avoid coupling at the N2 or N7 position. Furthermore, additional processing steps are required to obtain the desired product.

Therefore, there is a need in the art for a process for preparation of guanine based carbonucleoside that can lead to higher selectivity in coupling guanine at the N9 position and can also be stereoselective. In addition, there is a need in the art for a process that avoids use of protecting groups requiring different conditions for deprotection. Hence, there is a need in the art for a process where a final global deprotection can be performed in a single step.

SUMMARY OF THE INVENTION

In one aspect, the specification relates to a process for preparing a compound of formula 1, the process containing the steps of:
reacting a compound of formula 2 with a compound of formula 3 under Mitsunobu-type reaction condition to obtain a compound of formula 4;

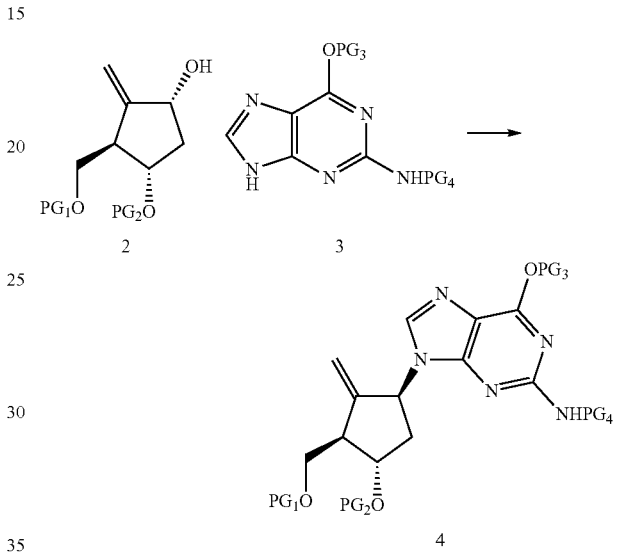

wherein $PG_1$, $PG_2$, $PG_3$ and $PG_4$ are protecting groups; deprotecting the compound of formula 4 to obtain the compound of formula 1

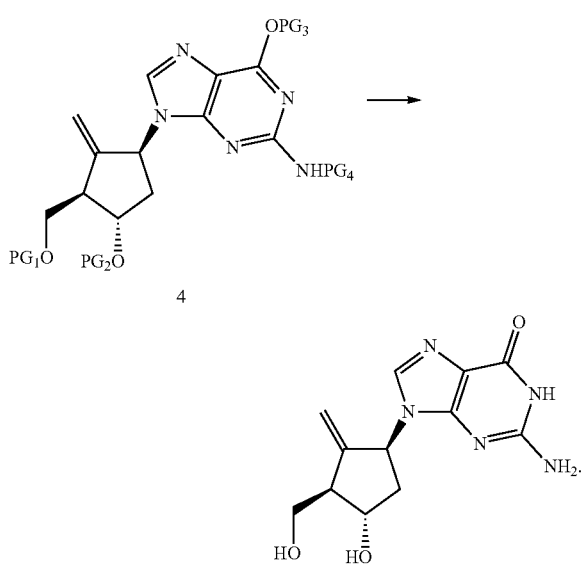

In another aspect, the specification relates to a compound of formula 4':

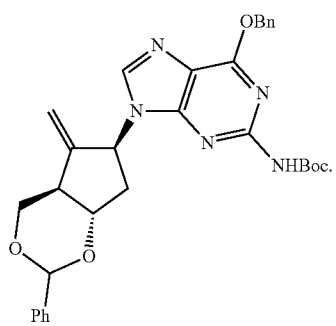

In a further aspect, the specification relates to a compound of formula 3':

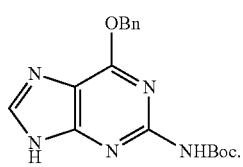

DETAILED DESCRIPTION

As noted above, the specification relates to a process for preparing a compound of formula 1, the process containing the steps of:

reacting a compound of formula 2 with a compound of formula 3 under Mitsunobu-type reaction condition to obtain a compound of formula 4;

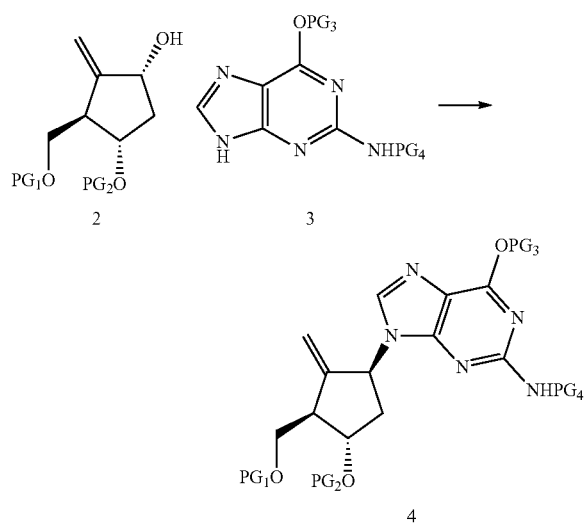

wherein $PG_1$, $PG_2$, $PG_3$ and $PG_4$ are protecting groups;

deprotecting the compound of formula 4 to obtain the compound of formula 1

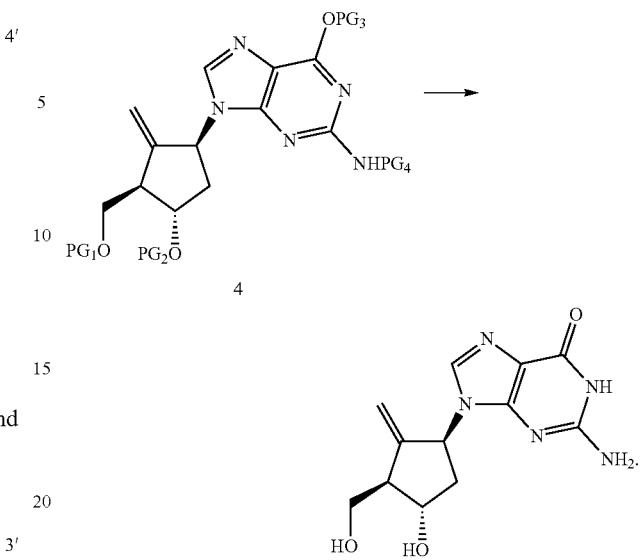

Compounds of formula 2 are disclosed in Canadian Patent Application No. 2,705,953. The compound of formula 3 can be obtained by protection of the oxygen atom at the 6-position of guanine followed by reacting with an amine protecting group to protect the N2-position to form the compound of formula 3.

The protecting groups in the process for obtaining the compound of formula 4 are not particularly limited. In one embodiment, for example and without limitation, each of the protecting groups selected for the compounds of formula 2 and 3 are the same or different and are acid labile protecting groups. An acid labile protecting group allows deprotection of the functional group by using an acid. By using acid labile protecting groups, a single one-pot deprotection step can be performed, preferably near the end of the synthesis to obtain the compound of formula 1.

The protecting groups $PG_1$, $PG_2$ and $PG_3$ for protecting the oxygen atoms in the compounds of formula 2 and 3 are not particularly limited and would be recognized by a person of skill in the art as being suitable for protection of a —OH substituent on an alkyl or ringed system. Moreover, such protecting groups can be removed (deprotection) using methods known to a person of skill in the art. Examples of suitable protecting groups can be found in the latest edition of Greene and Wats, *Protecting Groups in Organic Synthesis*. In one embodiment, for example and without limitation, the protecting group is acetyl, benzoyl, benzyl, β-methoxyethoxymethyl ether (MEM), dimethoxytrityl (DMT), methoxytrityl (MMT), trityl, methoxymethyl ether (MOM), p-methoxybenzyl ether (PMB), pivaloyl (Piv) or tetrahydropyranyl (THP). In another embodiment, the protecting groups $PG_1$ and $PG_2$ used for protecting the two hydroxyl groups in the compound of formula 2 together form an aldehyde or a ketone acetal. Using an aldehyde or a ketone can lead to formation of an acetal or ketal, which can be subsequently cleaved by using an acid. This procedure allows for a single protecting group for the two hydroxyl groups in the compound of formula 2. In a further embodiment, the aldehyde used for protecting the two hydroxyl groups in the compound of formula 2 is benzaldehyde. In a still further embodiment, the protecting group $PG_3$ on the oxygen atom in the compound of formula 3 is benzyl.

The protecting group PG₄ used for protecting the amine at the 2-position (N2) in guanine is not particularly limited and would be recognized by a person of skill in the art as being suitable for protection of a —NH₂ substituent on an alkyl or ringed system. Moreover, such protecting groups can be removed (deprotection) using methods known to a person of skill in the art. Examples of suitable protecting groups can be found in the latest edition of Greene and Wuts, *Protecting Groups in Organic Synthesis*. In one embodiment, for example and without limitation, the PG₄ protecting group is tert-butyloxycarbonyl (BOC), tosyl (Ts) or a silyl based protecting groups, such as, for example and without limitation, trimethylsilyl.

The compounds of formula 2 and 3 are reacted under Mitsunobu-type reaction conditions. A Mitsunobu reaction allows conversion of an alcohol into a different functional group, while undergoing inversion of stereochemistry. Therefore, the new functional group has the opposite stereochemistry to the stereochemistry of the alcohol. The reaction can involve use of a phosphine, such as an aryl phosphine or an alkyl phosphine, along with an azo-based compound in an appropriate solvent and reaction conditions.

The phosphine used for the Mitsunobu-type reaction is not particularly limited, and can be for example and without limitation, an alkyl phosphine or an aryl phosphine, as noted above. In one embodiment, for example and without limitation, the phosphine is triphenyl phosphine (PPh₃) or trimethylphosphine (PMe₃).

Azo based compounds used in Mitsunobu-type reactions are not particularly limited. In one embodiment, the azo-based compound is, for example and without limitation, diethylazodicarboxylate (DEAD), diisopropylazodicarboxylate (DIAD), di-t-butylazodicarboxylate, 2-(phenylazo)pyridine (azpy), di-p-chlorobenzylazodicarboxylate (DCAD) or 1,1'-(azodicarboxyl)dipiperidine (ADDP).

In another embodiment of the Mitsunobu-type reaction, a phosphorane ylide is utilized rather than a phosphine and azo-based compound. The phosphorane ylide is not particularly limited. In one embodiment, for example and without limitation, the phosphorane ylide is (cyanomethylene)trimethyl phosphorane or tributylphosphorane.

The solvent used for the Mitsunobu-type reaction is not particularly limited. In one embodiment, for example and without limitation, the solvent used for the Mitsunobu-type reaction is tetrahydrofuran, acetonitrile, dichloromethane, toluene, or a mixture thereof.

The temperature for carrying out the Mitsunobu-type reaction is also not particularly limited. In one embodiment, for example and without limitation, the temperature used for the Mitsunobu-type reaction is room temperature. In another embodiment, for example and without limitation, the reaction is carried out by refluxing the solvent. In further embodiment, for example and without limitation, the reaction is carried out by heating up to about 120° C., and all temperatures between room temperature and 120° C. In a further embodiment, for example and without limitation, the reaction is carried out by cooling the reaction up to about −20° C. and all temperature between room temperature and −20° C. The reaction temperature would depend upon the reagent used and the desired conditions.

The sequence of addition of the reagents for carrying out the Mitsunobu-type reaction is not particularly limited and should be known or can be determined by a person of skill in the art. In one embodiment, for example and without limitation, the compounds of formula 2 and 3 and the phosphine are dissolved in the solvent, followed by addition of the azo-based compound.

Using the process, as disclosed herein, can lead to a higher yield of the intermediate compound of formula 4 compared to when an unprotected N2-guanine has been used. The intermediate compound of formula 4 can then be deprotected, optionally, in a single step using a one-pot process to obtain the compound of formula 1. This can also lead to higher overall yield. Moreover, use of the compound of formula 3 can lead to higher regioselectivity of N9 versus N2, N7 or O6, which can improve the purity profile of compounds obtained in the process for preparing the compound of formula 1. Still further, use of the Mitsunobu type reaction conditions allows for inversion of stereochemistry, and hence control of the stereochemistry of the final product obtained.

EXAMPLES

The following examples are illustrative and non-limiting and represent specific embodiments of the present invention.

Example 1

Preparation of tert-Butyl-6-(benzyloxy)-9-((4aR,6S,7aS)-5-methylene-2-phenylhexahydrocyclopenta[d][1,3]dioxin-6-yl)-9H-purin-2-ylcarbamate (4')

To a round bottom flask was added 2 (250 mg, 1.08 mmol, 1 equiv), 3' (441 mg, 1.30 mmol, 1.2 equiv), triphenylphosphine (370 mg, 1.40 mmol, 1.3 equiv), and tetrahydrofuran (6 mL). The resulting suspension was stirred at room temperature for 10 min and diisopropyl azodicarboxylate (283 mg, 1.40 mmol, 1.3 equiv) was added dropwise over 10 min. Stirring was continued for an additional 30 min and then the reaction mixture was concentrated to dryness. The crude product was purified by flash column chromatography using 35% ethyl acetate/heptane to afford 465 mg of 4' as a white solid (78%). 1H NMR (300 MHz, CDCl₃) δ 7.77 (s, 1H), 7.54 (m, 4H), 7.30 (m, 6H), 7.27 (s, 1H), 5.86 (s, 1H), 5.60 (s, 2H), 5.50 (brd, 1H, J=9.5 Hz), 4.91 (m, 2H), 4.61 (m, 2H), 4.18 (t, 1H, J=10.6 Hz), 2.66 (brt, 1H, 8.6 Hz), 2.33-2.59 (m, 2H), 1.55 (s, 9H).

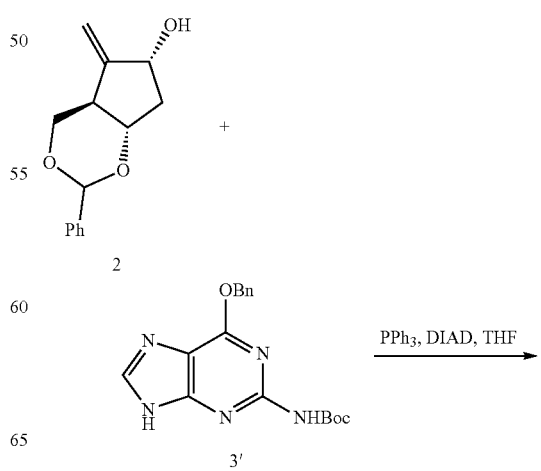

-continued

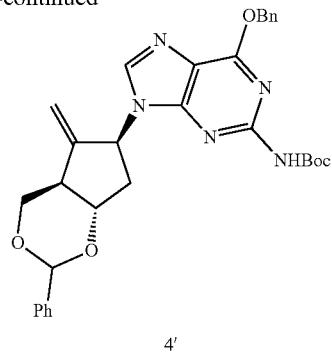

4'

Example 2

Preparation of 2-Amino-1,9-dihydro-9-((1S, 3R, 4S)-4-hydroxy-3-(hydroxymethyl)-2-methylenecyclopentyl)-6H-purin-6-one (1)

To a round bottom flask was added 4' (450 mg, 0.81 mmol, 1 equiv), dichloromethane (10 mL), and 2N aq HCl (5 mL). The resulting biphasic solution was stirred at room temperature over 18 h. The layers were separated and the aqueous layer was washed with dichloromethane (2×2 mL). To the aqueous layer was added charcoal (100 mg) and the mixture was stirred for 10 min and then filtered. 3N aq NaOH was added dropwise to the aqueous layer to a pH of 7-8. The resulting suspension was stirred at room temperature for 45 min, filtered, and washed with water (2 mL) to afford 120 mg of 1 as a white solid (50%), purity: >99.8%. 1H NMR (300 MHz, DMSO-d6) δ 10.57 (s, 1H), 7.67 (s, 1H), 6.42 (s, 2H), 5.36 (t, 3H, J=8.4 Hz), 5.10 (s, 1H), 4.88 (d, 1H, J=2.9 Hz), 4.85 (t, 1H, J=5.1 Hz), 4.56 (s, 1H), 4.23 (s, 1H), 3.53 (t, 2H, J=6.1 Hz), 2.50 (s, 1H).

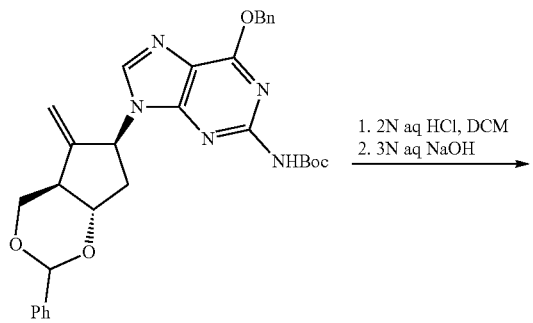

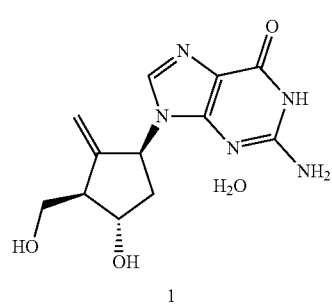

1

Example 3

Preparation of 6-(Benzyloxy)-9-((4aR,6S,7aS)-5-methylene-2-phenylhexahydrocyclopenta[d][1,3]dioxin-6-yl)-N-(trimethylsilyl)-9H-purin-2-amine (4")

To a round bottom flask was added 2 (700 mg, 3.01 mmol, 1 equiv), 3" (1.22 g, 3.16 mmol, 1.05 equiv), triphenylphosphine (1.03 g, 3.92 mmol, 1.3 equiv), and tetrahydrofuran (18 mL). The resulting suspension was stirred at room temperature for 10 min and diisopropyl azodicarboxylate (790 mg, 3.92 mmol, 1.3 equiv) was added dropwise over 10 min. Stirring was continued for an additional 2 h and then the reaction mixture was concentrated to dryness. The crude product was purified by flash column chromatography using 50% ethyl acetate/heptane to afford 540 mg of 4" as a white solid (34%). 1H NMR (300 MHz, CDCl3) δ 7.58 (s, 1H), 7.50 (m, 4H), 7.40 (m, 6H), 5.66 (s, 1H), 5.56 (s, 2H), 5.46 (brd, 1H, J=9.9 Hz), 4.95 (t, 1H, J=2.5 Hz), 4.75 (t, 1H, J=1.9 Hz), 4.65 (m, 2H), 4.24 (m, 1H), 4.05 (t, 1H, J=9.9 Hz), 2.68 (m, 1H), 2.47 (m, 2H), 0.31 (s, 9H).

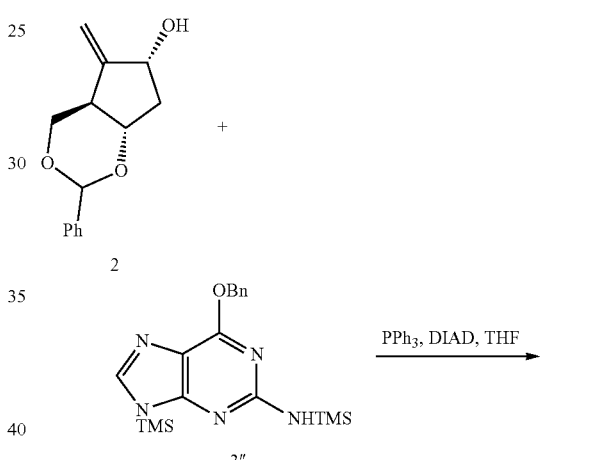

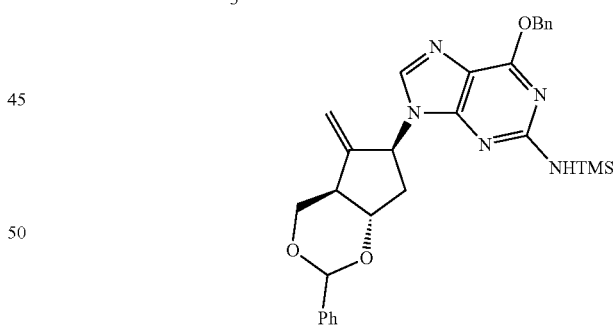

4"

Example 4

Preparation of 2-Amino-1,9-dihydro-9-((1S, 3R, 4S)-4-hydroxy-3-(hydroxymethyl)-2-methylenecyclopentyl)-6H-purin-6-one (1)

To a round bottom flask was added 4" (470 mg, 0.89 mmol, 1 equiv), dichloromethane (7 mL), and 2N aq HCl (5 mL). The resulting biphasic solution was stirred at room temperature over 18 h. The layers were separated and the aqueous layer was washed with dichloromethane (2×3 mL). To the aqueous layer was added charcoal (50 mg) and the mixture was stirred for 2 h and then filtered. 3N aq NaOH was added dropwise to the aqueous layer to a pH of 7-8. The resulting suspension was stirred at room temperature for 1 h, filtered, and washed with water (2 mL) to afford 230 mg of 1 as a white solid (88%), purity: >99.8%. 1H NMR (300 MHz, DMSO-d6) δ 10.57 (s, 1H), 7.67 (s, 1H), 6.42 (s, 2H), 5.36 (t, 3H, J=8.4 Hz), 5.10 (s, 1H), 4.88 (d, 1H, J=2.9 Hz), 4.85 (t, 1H, J=5.1 Hz), 4.56 (s, 1H), 4.23 (s, 1H), 3.53 (t, 2H, J=6.1 Hz), 2.50 (s, 1H).

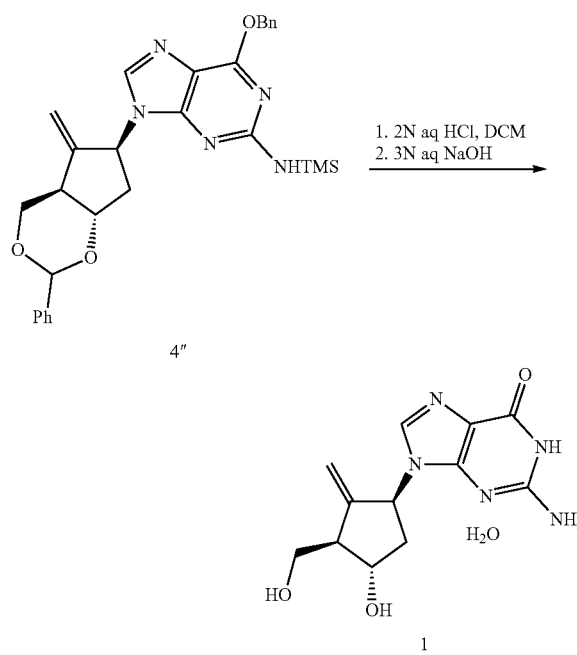

The invention claimed is:

1. A process for preparing a compound of formula 1, the process comprising the steps of:
i) reacting a compound of formula 2 with a compound of formula 3 under Mitsunobu-type reaction conditions to obtain a compound of formula 4;

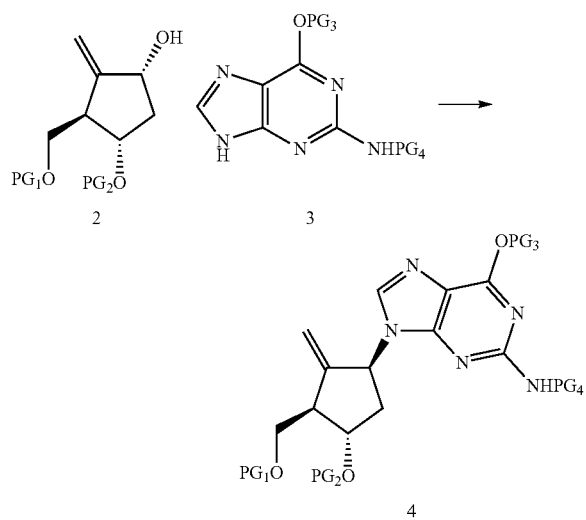

wherein $PG_1$, $PG_2$, $PG_3$ and $PG_4$ are protecting groups and are the same or different;

ii) deprotecting the compound of formula 4 to obtain the compound of formula 1

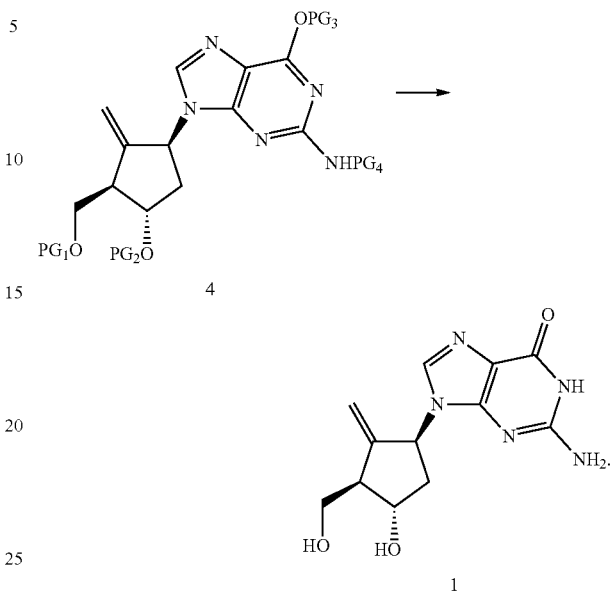

2. The process according to claim 1, wherein the Mitsunobu type reaction condition comprises an alkyl phosphine or an aryl phosphine, and an azo-based compound.

3. The process according to claim 2, wherein the alkyl phosphine is $PMe_3$.

4. The process according to claim 2, wherein the aryl phosphine is $PPh_3$.

5. The process according to claim 2, wherein the azo based compound is selected from the group consisting of diethylazodicarboxylate (DEAD), diisopropylazodicarboxylate (DIAD), di-t-butylazodicarboxylate, 2-(phenylazo)pyridine (azpy), di-p-chlorobenzylazodicarboxylate (DCAD), and 1,1'-(azodicarboxyl)dipiperidine (ADDP).

6. The process according to claim 2, wherein the azo based compound is diisopropylazodicarboxylate (DIAD).

7. The process according to claim 1, wherein the Mitsunobu type reaction condition comprises a phosphorane ylide.

8. The process according to claim 7, wherein the phosphorane ylide is selected from the group consisting of (cyanomethylene)trimethyl phosphorane and tributylphosphorane.

9. The process according to claim 1, wherein the solvent for the Mitsunobu type reaction is selected from the group consisting of tetrahydrofuran, acetonitrile, dichloromethane, toluene, and mixtures thereof.

10. The process according to claim 1, wherein the solvent for the Mitsunobu type reaction is tetrahydrofuran.

11. The process according to claim 1, wherein the Mitsunobu type reaction is carried out at room temperature.

12. The process according to claim 1, wherein the protecting groups on the compound of formula 2 and 3 are acid labile protecting groups.

13. The process according to claim 1, wherein each protecting group $PG_1$ and $PG_2$ present on the oxygen atom in the compound of formula 2, independently, is selected from the group consisting of acetyl, benzoyl, benzy, β-methoxyethoxymethyl ether (MEM), dimethoxytrityl (DMT), methoxytrityl (MMT), trityl, methoxymethyl ether (MOM), p-methoxybenzyl ether (PMB), pivaloyl (Piv), and tetrahydropyranyl (THP).

14. The process according to claim 1, wherein the protecting groups $PG_1$ and $PG_2$ used for protecting the two oxygen atoms in the compound of formula 2 together form an aldehyde or a ketone acetal.

15. The process according to claim 14, wherein the aldehyde acetal is benzaldehyde acetal.

16. The process according to claim 1, wherein the protecting group $PG_3$ on the oxygen atom in the compound of formula 3 is selected from the group consisting of acetyl, benzoyl, benzyl, β-methoxyethoxymethyl ether (MEM), dimethoxytrityl (DMT), methoxytrityl (MMT), trityl, methoxymethyl ether (MOM), p-methoxybenzyl ether (PMB), pivaloyl (Piv), and tetrahydropyranyl (THP).

17. The process according to claim 16, wherein the protecting group $PG_3$ on the oxygen atom in the compound of formula 3 is benzyl.

18. The process according to claim 1, wherein the protecting group $PG_4$ on the nitrogen atom in the compound of formula 3 is selected from the group consisting of tert-butyloxycarbonyl (BOC), tosyl (Ts) and a silyl based protecting group.

19. The process according to claim 1, wherein the protecting group $PG_4$ on the nitrogen atom in the compound of formula 3 is tert-butyloxycarbonyl (BOC).

20. The process according to claim 1, wherein step (ii) of the process for deprotecting the compound of formula 4 is carried out in a one pot process.

21. The process according to claim 1, wherein step (ii) of the process for deprotecting the compound of formula 4 is carried out in as a multi-step process.

22. The process according to claim 1, wherein the compound of formula 1 has a purity of at least 99.8%.

\* \* \* \* \*